United States Patent [19]

Harris, II et al.

[11] 4,161,176

[45] Jul. 17, 1979

[54] COLOR ADAPTABLE BANDAGE

[75] Inventors: Frederick E. Harris, II, 944 Palisades Beach Rd., Santa Monica, Calif. 90403; William H. Pavitt, Jr., Pacific Palisades, Calif.

[73] Assignee: Frederick Earl Harris, II, Santa Monica, Calif.

[21] Appl. No.: 784,701

[22] Filed: Apr. 5, 1977

[51] Int. Cl.² .............................................. A61L 15/00
[52] U.S. Cl. ...................................... 128/155; 128/156
[58] Field of Search ................................. 128/155, 156

[56] References Cited

U.S. PATENT DOCUMENTS

| | | | |
|---|---|---|---|
| 2,905,174 | 9/1959 | Smith | 128/156 |
| 3,687,136 | 8/1972 | Carmody | 128/156 |
| 4,094,316 | 6/1978 | Nathanson | 128/156 |

Primary Examiner—John D. Yasko
Attorney, Agent, or Firm—Smyth, Pavitt, Siegemund, Jones & Martella

[57] ABSTRACT

A bandage having several "peel-off" outer layers of various colors to permit selection of a color pleasing to the wearer. The selection is effected by peeling off any overlying layers not desired, to expose the layer of preferred color. In one embodiment, the colors of the layers are chosen to approximate certain human skin colors.

8 Claims, 5 Drawing Figures

U.S. Patent  Jul. 17, 1979  4,161,176
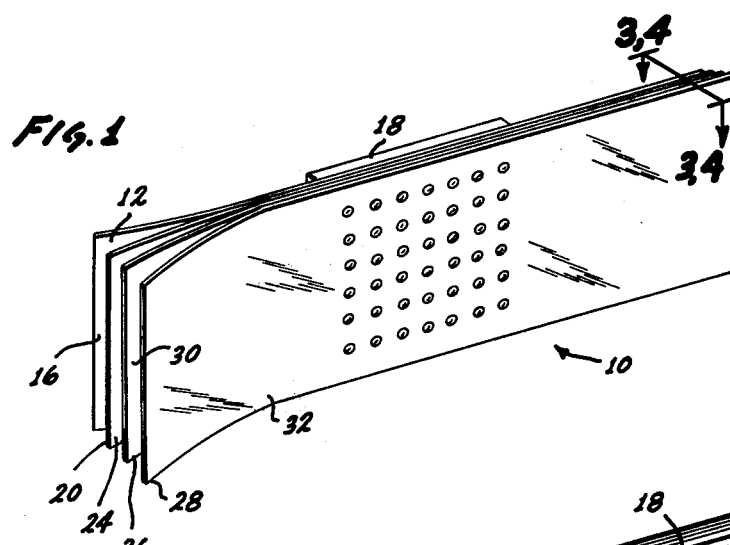
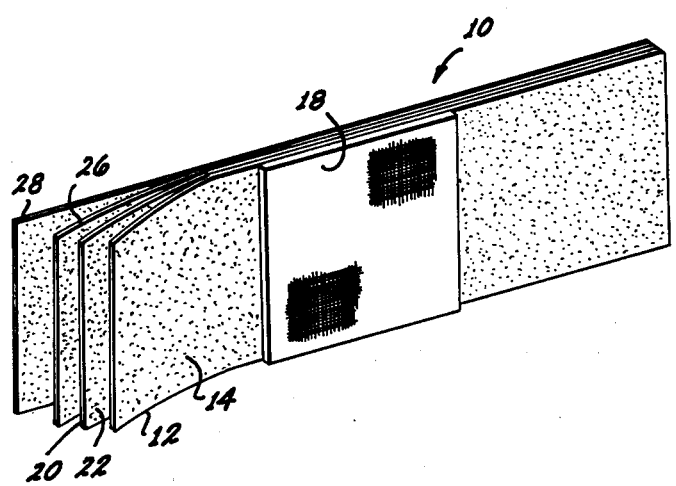
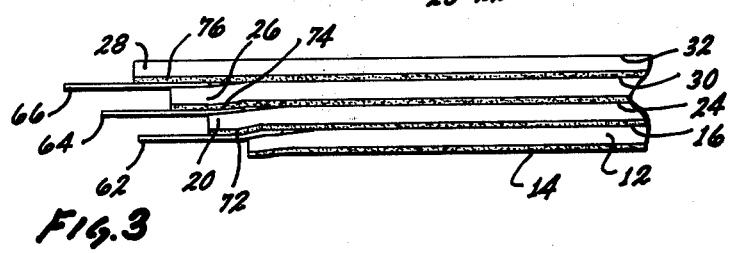
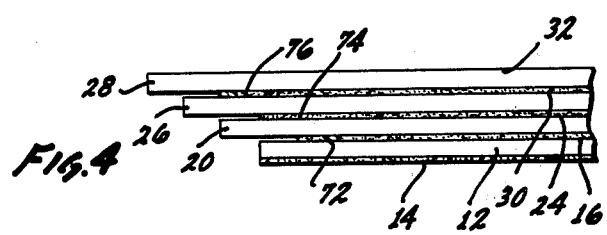
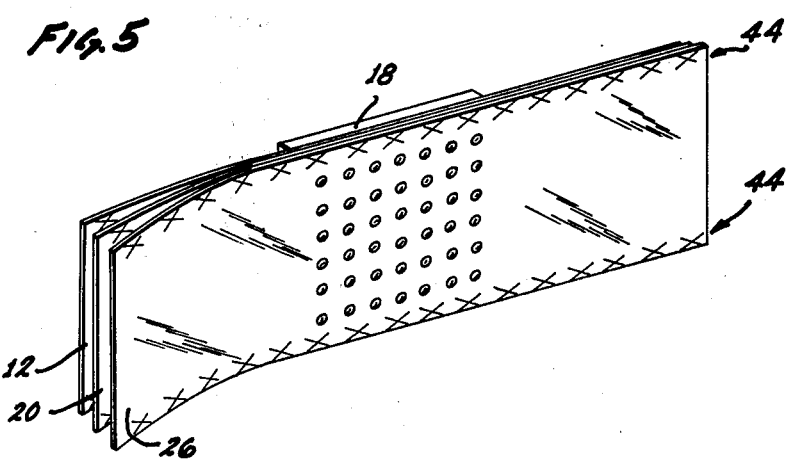

COLOR ADAPTABLE BANDAGE

The present invention is a bandage in which the color of the exposed portion can be selected by the wearer.

During the past several decades, many inventors have been concerned with rendering less obvious the fact that a person is wearing a bandage. Generally, these inventors have taken two approaches.

One approach has been to provide a bandage which is transparent so that the color of the skin of the wearer will tend to be visible through all or most of the bandage. This approach is illustrated in U.S. Pat. No. 3,425,412 issued to Pope Feb. 4, 1969; in U.S. Pat. No. 2,254,883 issued to Boyle on Sept. 2, 1941; U.S. Pat. No. 2,734,503 issued to Doyle Feb. 14, 1956; U.S. Pat. No. 2,226,546 issued Dec. 31, 1940 to Bowar; U.S. Pat. No. 2,273,873 issued Feb. 24, 1942 to Klein; and U.S. Pat. No. 2,164,360 issued July 4, 1939 to Strauch.

A second approach found in the prior art is to attempt to provide some type of coloring in the bandage which approximates the color of the skin of the wearer. This approach is illustrated in: U.S. Pat. No. 1,967,923 issued July 24, 1934 to Connolly; in U.S. Pat. No. 2,824,559 issued Feb. 25, 1958 to Sullivan; in U.S. Pat. 2,905,174 issued Sept. 22, 1959 to Smith; and in U.S. Pat. No. 3,687,136 issued Aug. 29, 1972 to Carmody.

The patent of Carmody appears to be the most pertinent to the present invention. In the Carmody patent, a transparent strip is employed, the opposite ends of which are coated with a pressure sensitive adhesive. An absorbent pad is disposed between the ends of the transparent strip. A second strip of suitable color is disposed between the transparent strip and the absorbent pad. Thus, as far as the ends of the strip are concerned, Carmody uses the transparency approach but he then attempts to cover the pad from view by some type of colored strip which approximates the skin color of the wearer.

Summarizing the prior art approaches, when a transparent strip is used, there remains the problem of concealing the absorbent pad and if an opaque bandage is used, there remains the problem of providing an appropriate range of colors.

In the present invention, this problem is solved by providing the bandage with several "peel off" outer layers of various colors. The wearer can select the color he desires by peeling off any overlying layers not desired, to expose that color which he deems most aesthetic. The "peel off" layers are attached to the basic bandage in a preferred embodiment by an adhesive coating applied to a portion of the surface of each peelable layer, while in alternative embodiments, the successive layers may be crimped together.

Several embodiments of the present invention are shown, by way of example, in the accompanying figures, in which:

FIG. 1 shows a perspective view of the bandage of the present invention as viewed from its normally-exposed side;

FIG. 2 is a perspective view of a preferred embodiment as seen from the side applied to the wearer's skin;

FIGS. 3 and 4 are edge views of the bandage shown in FIG. 1 taken in the direction indicated in FIG. 1 and showing alternative techniques to facilitate separation of layers;

FIG. 5 is a perspective view of an alternative embodiment in which the layers are crimped together.

Turning now to FIG. 1, the bandage 10 of the present invention is seen to include a first patch of film 12 which has an adhesive coating 14 on a first side of it, which is the side normally in contact with the skin of the wearer. The second side 16 of the first patch 12 is non-adhesive. The film may be cut of any appropriate material, and such materials are well known in the art. The word film as used herein is defined broadly to include tapes and fabrics as well as compressed fibers, although a plastic film is used in the preferred embodiment.

In the preferred embodiment shown in FIGS. 1 and 2, a pad 18 of dressing material is affixed to the adhesive-coated first side of the first patch 12. The dressing material, in a preferred embodiment is formed of knit, woven, or compressed fibers, and in some embodiments is treated with an antiseptic.

The bandage of the preferred invention shown in FIGS. 1 and 2 further includes a first peelable patch of film 20 of substantially the same size and shape as the first patch of film 12. This additional patch of film 20 has a first side 22 on which an adhesive coating is applied and has a second side 24 which is non-adhesive. The additional patch of film 20 is removably attached to the first patch 20 facing the second surface of the first patch 12. The second side 24 of the additional patch 20 is a different color from the second side 16 of the first patch 12.

Additional patches of film 26, 28 may also be removably attached to the first patch of first film 12 and they are similiar to the first additional patch 20 except for the color of their second surfaces 30, 32.

The adhesive coating on the first side of the additional patches of film do not necessarily cover the entire area of the first surfaces. For example, the coating may be applied in the form of a relatively narrow strip extending along the longer edges of the additional patches of film. In the alternative embodiment shown in FIG. 5, no adhesive coating is applied to the additional patches of film, but instead they are removably attached to the first patch of film 12 by a crimp 44 extending along at least a portion of the edges of the bandage.

As noted above, the second sides 16,24,30,32 of the first patch of film and of the additional patches of film 20, 26, 28 have different colors. The wearer selects the color he desires by peeling off any overlying layers of undesirable color, leaving the patch of desired color attached to the first patch.

Separation of the additional patches from one another or from the first patch 12 can be facilitated by the techniques shown in FIG. 3 and FIG. 4. These Figures show the edge of the bandage very greatly magnified.

In the preferred embodiment of FIG. 3, narrow strips 62,64,66 of a non-adhesive paper or plastic material extend along the edge of each of the additional strips 20,26,28 respectively. The non-adhesive strips 62,64,66 adhere to the adhesive coating 72,74,76 on the additional strips 20,26,28 respectively. In a preferred embodiment, the colors of the strips 62,64,66 match the colors of the additional patches 20,26,28 respectively. Because the strips 62,64,66 do not adhere to the second surfaces 16,24,30 of the patches 12,20,26 separation of one or more patches may be effected by lifting and pulling the appropriate strip. In the preferred embodiment, successive ones of the strips 62,64,66 extend successively farther so that each of them conceals the underlying ones.

In the alternative embodiment shown in FIG. 4, the adhesive coatings 72,74,76 do not extend to the ends of the patches, and therefore the ends may be separated readily to effect removal of unwanted patches.

Numerous other variations and embodiments will undoubtedly be apparent to those skilled in the art, and these variations are within the scope of the present invention which is limited only by the following claims.

What is claimed is:

1. A bandage comprising:
   a first patch of opaque film having an adhesive coating on a first side and being non-adhesive on its second side;
   at least one additional opaque patch of film, large enough to cover the non-adhesive second side of said first patch of opaque film and removably attached to it, having a first side facing the second side of said first patch of film, and having a second side;
   the second sides of said first and additional opaque patches of film having different colors.

2. The bandage of claim 1 further comprising:
   a pad of dressing material fastened to the adhesive-coated first side of said first patch of opaque film.

3. The bandage of claim 1 wherein said additional patches of opaque film each have an adhesive coating on their first sides.

4. The bandage of claim 3 wherein each of said additional patches of opaque film further comprises a non-adhesive tab affixed to its first side by the adhesive coating, said tab disposed to overlap portion of the periphery of the additional patch to which it is affixed.

5. The bandage of claim 4 wherein the edges of successive additional patches of opaque film are staggered slightly in one direction.

6. The bandage of claim 3 wherein a portion of the first side adjacent the edge of each additional patch of opaque film is free of adhesive coating, whereby separation of the additional layers is facilitated.

7. The bandage of claim 6 wherein the edges of successive additional patches of opaque film are staggered slightly in one direction.

8. The bandage of claim 1 wherein said colors substantially match predetermined different colors of human skin.

* * * * *